United States Patent [19]
Fuisz

[11] Patent Number: 5,624,684
[45] Date of Patent: *Apr. 29, 1997

[54] ENZYME SYSTEMS

[75] Inventor: Richard C. Fuisz, Great Falls, Va.

[73] Assignee: Fuisz Technologies Ltd., Chantilly, Va.

[*] Notice: The term of this patent shall not extend beyond the expiration date of Pat. No. 5,578,730.

[21] Appl. No.: 150,045

[22] PCT Filed: May 13, 1992

[86] PCT No.: PCT/US92/04048

§ 371 Date: Nov. 17, 1993

§ 102(e) Date: Nov. 17, 1993

[87] PCT Pub. No.: WO92/20329

PCT Pub. Date: Nov. 26, 1992

Related U.S. Application Data

[63] Continuation-in-part of Ser. No. 702,068, May 17, 1991, abandoned.

[51] Int. Cl.$^6$ .............. A61K 9/14; A61K 35/70; A61K 35/72; A61K 35/74; A61K 38/43; A21D 8/04; A23C 9/12; C11D 3/386

[52] U.S. Cl. .............. 424/484; 424/486; 424/487; 424/488; 424/489; 424/499; 424/501; 426/19; 426/42; 426/61; 426/62; 426/63; 426/443; 426/583; 426/549; 426/465; 426/7; 510/530; 510/392; 428/402

[58] Field of Search .............. 424/484, 486–488, 424/499, 501, 489; 252/174.12, DIG. 12; 426/549, 583; 428/402

[56] References Cited

U.S. PATENT DOCUMENTS

| | | |
|---|---|---|
| Re. 32,016 | 10/1985 | Esders et al. ............... 435/28 |
| 2,826,169 | 3/1958 | Le Veen . |
| 2,918,404 | 12/1959 | Mende ............... 167/58 |
| 3,019,745 | 2/1962 | Du Bois ............... 107/8 |
| 3,036,532 | 5/1962 | Bowe ............... 107/8 |
| 3,067,743 | 12/1962 | Merton et al. ............... 128/270 |
| 3,070,045 | 12/1962 | Bowe ............... 107/8 |
| 3,073,262 | 1/1963 | Bowe ............... 107/8 |
| 3,095,258 | 6/1963 | Scott ............... 18/54 |
| 3,118,396 | 1/1964 | Brown et al. ............... 107/8 |
| 3,131,428 | 5/1964 | Mika ............... 18/8 |
| 3,308,221 | 3/1967 | Opfell ............... 264/174 |
| 3,324,061 | 6/1967 | Tanquary et al. ............... 260/29.2 |
| 3,482,998 | 12/1969 | Carroll et al. ............... 99/108 |
| 3,523,889 | 8/1970 | Eis ............... 210/20 |
| 3,557,717 | 1/1971 | Chivers ............... 107/54 |
| 3,595,675 | 7/1971 | Ash et al. ............... 99/130 |
| 3,615,671 | 10/1971 | Schoaf ............... 99/78 |
| 3,625,214 | 12/1971 | Higuchi ............... 128/260 |
| 3,676,148 | 7/1972 | De Weese et al. ............... 99/1 |
| 3,686,000 | 8/1972 | Lawrence ............... 99/134 |
| 3,723,134 | 3/1973 | Chivers ............... 99/134 |
| 3,749,671 | 7/1973 | Gedge, III et al. ............... 252/89 |
| 3,762,846 | 10/1973 | Chivers ............... 425/7 |
| 3,766,165 | 10/1973 | Rennhard ............... 260/209 |
| 3,856,443 | 12/1974 | Salvi ............... 425/9 |
| 3,875,300 | 4/1975 | Homm et al. ............... 424/28 |
| 3,876,794 | 4/1975 | Rennhard ............... 426/152 |
| 3,907,644 | 9/1975 | Mollering et al. ............... 195/99 |
| 3,912,588 | 10/1975 | Mollering et al. ............... 195/29 |
| 3,925,164 | 12/1975 | Beaucamp et al. ............... 195/103.5 |
| 3,925,525 | 12/1975 | La Nieve ............... 264/40 |
| 3,930,043 | 12/1975 | Warning et al. ............... 426/515 |
| 3,951,821 | 4/1976 | Davidson ............... 252/1 |
| 3,967,623 | 7/1976 | Butterworth et al. ............... 128/287 |
| 3,972,725 | 8/1976 | Nicol ............... 127/58 |
| 3,981,739 | 9/1976 | Dmitrovsky et al. ............... 127/60 |
| 3,992,265 | 11/1976 | Hansen ............... 195/127 |
| 4,056,364 | 11/1977 | Dmitrovsky et al. ............... 23/273 |
| 4,072,658 | 2/1978 | Okamoto et al. ............... 260/49 |
| 4,086,418 | 4/1978 | Turbak ............... 539/30 |
| 4,090,920 | 5/1978 | Studer, Jr. ............... 195/127 |
| 4,136,145 | 1/1979 | Fuchs et al. ............... 264/164 |
| 4,153,512 | 5/1979 | Messner et al. ............... 195/103.5 K |
| 4,159,210 | 6/1979 | Chen et al. ............... 127/29 |
| 4,160,696 | 7/1979 | Wu ............... 435/25 |
| 4,164,448 | 8/1979 | Roeschlau et al. ............... 435/11 |
| 4,168,205 | 9/1979 | Danninger et al. ............... 435/10 |
| 4,186,251 | 1/1980 | Tarbutton ............... 435/11 |
| 4,194,063 | 3/1980 | Frank et al. ............... 435/12 |

(List continued on next page.)

FOREIGN PATENT DOCUMENTS

| | | |
|---|---|---|
| 609137 | 4/1988 | Australia . |
| 609135 | 4/1988 | Australia . |
| 900605 | 11/1977 | Belgium . |
| 1303511 | 4/1988 | Canada . |
| 0287488A1 | 3/1988 | European Pat. Off. . |
| 0387950A1 | 8/1990 | European Pat. Off. . |
| 88/2770 | 4/1988 | South Africa . |
| 88/2771 | 4/1988 | South Africa . |
| 89/9318 | 12/1989 | South Africa . |
| 90/2139 | 3/1990 | South Africa . |
| 90/8406 | 8/1991 | South Africa . |
| 519858 | 4/1971 | Switzerland . |
| 489211 | 7/1986 | Switzerland . |
| 1224947 | 3/1971 | United Kingdom . |
| 2155934 | 3/1985 | United Kingdom . |
| WO91/18613 | 5/1991 | WIPO . |

OTHER PUBLICATIONS

R.H. Doremus, "Crystallization of Sucrose From Aqueous Solution," *Journal of Colloid and Interface Science*, 104, pp. 114–120 (1985).

P. Bennema, "Surface Diffusion and the Growth of Sucrose Crystals," *Journal of Crystal Growth*, 3,4 pp. 331–334 (1968).

(List continued on next page.)

*Primary Examiner*—Edward J. Webman
*Attorney, Agent, or Firm*—Hoffmann & Baron

[57] ABSTRACT

Enzyme products are disclosed. The enzyme products include an enzyme-bearing matrix formed by subjecting a feedstock containing enzyme(s) and carrier materials to conditions which alter the physical and/or chemical structure of the carrier. The matrix suspends the enzyme for protection, delivery, dispersion and activation at the desired time and under selected conditions. Methods of producing the enzyme carrying matrix and enhanced enzyme products are also disclosed.

34 Claims, No Drawings

U.S. PATENT DOCUMENTS

| | | | |
|---|---|---|---|
| 4,241,178 | 12/1980 | Esders et al. | 435/15 |
| 4,293,570 | 10/1981 | Vadasz | 426/3 |
| 4,303,684 | 12/1981 | Pitchon et al. | 426/312 |
| 4,335,232 | 6/1982 | Irwin | 528/128 |
| 4,338,350 | 7/1982 | Chen et al. | 426/658 |
| 4,348,420 | 9/1982 | Lynch et al. | 426/272 |
| 4,362,757 | 12/1982 | Chen et al. | 426/599 |
| 4,371,516 | 2/1983 | Gregory et al. | 424/22 |
| 4,376,743 | 3/1983 | Dees | 264/103 |
| 4,382,963 | 5/1983 | Klose et al. | 426/3 |
| 4,492,685 | 1/1985 | Keith et al. | 424/28 |
| 4,496,592 | 1/1985 | Kuwahara et al. | 426/5 |
| 4,500,546 | 2/1985 | Turbak et al. | 514/781 |
| 4,511,584 | 4/1985 | Percel et al. | 426/99 |
| 4,526,525 | 7/1985 | Oiso et al. | 425/9 |
| 4,585,797 | 4/1986 | Cioca | 514/773 |
| 4,619,833 | 10/1986 | Anderson | 426/548 |
| 4,765,991 | 8/1988 | Cherukuri | 426/3 |
| 4,772,477 | 9/1988 | Weiss et al. | 426/99 |
| 4,793,782 | 12/1988 | Sullivan | 425/7 |
| 4,855,326 | 8/1989 | Fuisz | 514/777 |
| 4,871,501 | 10/1989 | Sugimoto | 264/211.22 |
| 4,872,821 | 10/1989 | Weiss | 425/9 |
| 4,879,108 | 11/1989 | Yang et al. | 424/440 |
| 4,885,281 | 12/1989 | Hanstein et al. | 514/53 |
| 4,978,537 | 12/1990 | Song | 426/5 |
| 4,997,856 | 3/1991 | Fuisz | 514/777 |
| 5,011,532 | 4/1991 | Fuisz | 106/215 |
| 5,028,632 | 7/1991 | Fuisz | 514/772 |
| 5,037,662 | 8/1991 | Poulose et al. | 426/52 |
| 5,039,446 | 8/1991 | Estell | 252/174.12 |
| 5,041,377 | 8/1991 | Becker et al. | 435/220 |
| 5,066,218 | 11/1991 | Silver | 426/20 |
| 5,073,387 | 12/1991 | Whistler | 426/7 |
| 5,082,682 | 1/1992 | Peterson | 426/564 |
| 5,082,684 | 1/1992 | Fung | 426/602 |
| 5,084,295 | 1/1992 | Whelan et al. | 426/565 |
| 5,089,606 | 2/1992 | Cole et al. | 536/54 |
| 5,094,872 | 3/1992 | Furcsik et al. | 426/578 |
| 5,096,492 | 3/1992 | Fuisz | 106/215 |
| 5,173,322 | 12/1992 | Melachouris et al. | 426/580 |
| 5,196,199 | 3/1993 | Fuisz | 424/401 |
| 5,238,696 | 8/1993 | Fuisz | 426/565 |
| 5,279,849 | 1/1994 | Fuisz | 426/658 |
| 5,286,513 | 2/1994 | Fuisz | 426/641 |
| 5,288,508 | 2/1994 | Fuisz | 426/5 |

OTHER PUBLICATIONS

T.D. Simpson, et al., "Crystalline Forms of Lactose Produced in Acidic Alcoholic Media," *Journal of food Science*, 47, pp. 1948–1954 (1982).

A.D. Randolph, et al., "Continuous Sucrose Nucleation," *The International Sugar Journal*, pp. 8–12 (1974).

K.B. Domovs, et al., "Methanol–Soluble Complexes of Lactose and of other Carbohydrates," *J. Dairy Science*, 43, pp. 1216–1223 (1960).

A.D. Randolph, et al., "Continuous Sucrose Nucleation," *The International Sugar Journal*, pp. 35–38 (1974).

A.D. Randolph, et al., "Continuous Sucrose Nucleation," *The International Sugar Journal*, pp. 73–77 (1974).

ICI Americas Inc., "ICI Americas Products for Cosmetics and Pharmaceuticals," (1977).

Domino Sugar Corporation, "Co–crystallization".

Domino Sugar Corporation, "Raspberry.".

Domino Sugar Corporation, "Molasses Dark".

ENZYME SYSTEMS

BACKGROUND OF THE INVENTION

The present application is a Continuation-In-Part of U.S. patent application Ser. No. 07/702,068 filed on May 17, 1991, now abandoned.

The present invention relates to new enzyme products. In particular, the invention relates to improved enzyme products such as leavening agents, alcohol fermenters, detergent ingredients, degradation agents, diagnostic agents, bioremediation agents, catalases and oxidases.

Enzymes are proteins which catalyze many biological reactions. As a result of their extraordinary catalytic power and specificity, enzymes have been used to speed up processes that would not otherwise occur. Many isolated enzymes are relatively unstable, often gradually lose activity prior to use, and may be easily inhibited by many factors.

Over the years, a number of enzyme products have been developed for a variety of purposes. For example, foods, detergents, cosmetics and pharmaceuticals have all been enhanced by enzymes. Many commercially prepared enzyme-based products, however, have certain drawbacks.

As an illustration, detergent enzymes, are usually produced in powdered or liquid form. They are difficult to handle, may cause an irritating dust, may be incompatible with other detergent products, and may deteriorate in the presence of moisture. The activity of enzymes in liquid detergents, which contain high levels of water and surfactants, tends to decrease over time. Frequently, the surfactants inactivate the enzymes. Consequently, there is a need to prepare enzyme products suitable for detergents which are easy to handle, do not cause irritation to users, and can be distributed uniformly in the detergent without reduced activity.

Similarly, it is important to be able to deliver and activate leavening agents and alcohol fermenters at the desired time and location in a biomass. For example, yeast has a tendency to "clump" together in aggregates which resist being dispersed during mixing. This "clumping" occurs with both dry formulations and paste formulations of yeast when added to dough or to a biomass. Thus, it would be beneficial to be able to suspend agents, such as yeast, in a medium for delivery and release as desired. This is especially true when the receiving material is an extensive mass, such as dough in baking and the biomass in fermentation procedures.

Other enzyme-bearing products can benefit from enhanced shelf-life. At room temperature enzymes used as indicators in immuneassays frequently experience short shelf-like. Horseradish peroxidase, lipoprotein lipase, glycerol-3-phosphate oxidase are ordinarily stored as freeze-dried powders at −20° C. Commonly-used assays are conducted in the range of 20°–30° C. It is thus important to provide a matrix which can improve the shelf life of enzymes used in immunoassays without impairing their activity.

There have been attempts in the past to deal with the problems associated with the use of enzymes. In U.S. Pat. No. 3,095,358, sorbitol is used to stabilize aqueous solutions containing papain, proteases and amylases. This method requires large amounts of stabilizing agent and is, therefore, expensive.

In U.S. Pat. No. 3,296,094, partially hydrolyzed and solubilized collagen and glycerol are used to stabilize aqueous solutions of proteolytic enzymes. This method requires large quantities of glycerol and, therefore, adds significantly to the cost of the enzyme solution.

U.S. Pat. No. 3,749,671 discloses a method of preparing enzyme-containing prills for use in laundry detergents. The disclosed prilling method requires the following steps: (a) heating a normally solid translucent material to a temperature sufficient to melt the material but insufficient to destroy the activity of the enzyme; (b) forming a slurry of the melted material and the enzyme; (c) injecting an inert gas into the slurry to form a uniform dispersion with the gas; and (d) forming prills from the resulting slurry. This method has many steps which require energy, equipment, and manual labor.

Although the methods discussed above represent efforts to improve enzyme-containing detergent products, the problems associated with the decreases in enzyme activity over time and adequate dispersal have not been solved.

It is, therefore, an object of this invention to provide an enzyme product which disperses or dissolves uniformly in the target liquid while retaining the enzyme activity for prolonged periods of time prior to use.

It is another object of this invention to provide a matrix which facilitates mixing an enzyme with a mass so that the enzyme can be dispersed efficiently throughout the mass.

It is yet another object of this invention to provide an enzyme product that exhibits an enhanced shelf life.

Other and further objects of the present invention will become apparent the following description and its scope will be pointed out with the appended claims.

SUMMARY OF THE INVENTION

The present invention includes an enzyme product which contains a matrix formed by subjecting a feedstock containing an enzyme and a carrier material to conditions of temperature and shear sufficient to produce the matrix which suspends the enzyme for storage and use. The carrier material undergoes transformation during processing in which its physical and/or chemical structure is altered.

"Enzyme product" in the present invention means a product which includes one or more enzymes. A nonlimiting list of enzymes which can be suspended in the matrix includes amylases, proteases, invertases, glucose oxidases, pectinases, lipases, lactases, and cellulases. The enzymes make up from about 1% to about 30% by weight of the matrix, with amounts of from about 5% to about 25% being preferred and the amounts are from about 10% to about 20% being most preferred.

Carrier materials which can be used for the matrix are saccharides, thermoplastic polymers, biodegradable polymers and water soluble cellulosic materials. The saccharides may be sucrose, lactose, fructose, dextrose, sorbitol, mannitol, maltose and mixtures thereof. The saccharides may also be selected from polydextrins, maltodextrins, and mixtures thereof. Thermoplastic polymers include polypropylene, polystyrene, polyethylene, polyvinylacetate, polyvinylalcohol, poly (methyl methacrylate), polyacrylic resins, lactide/glycolide copolymer and mixtures thereof. Biodegradable polymers include poly(cis-isoprene) aliphatic polyesters, polyurethanes and urea-formaldehyde polymers. The cellulosic materials are water soluble and include methyl cellulose, ethyl cellulose, hydroxymethyl cellulose, ethyl cellulose, alkali metal salts of carboxy methyl cellulose and mixtures thereof.

As a result of the present invention, enzymes can be suspended, protected, dispersed and generally engineered for selective delivery at desired sites under selected conditions. Various enzyme products can be provided which disperse or dissolve uniformly in the target liquid, biomass, etc. The enzyme products of this invention can also be designed to retain their activity for long periods of time prior to use. A non-inclusive list of uses for the matrix of the invention includes leavening agents, ,alcohol fermenters, detergents, digestive aid products, clinical diagnostic agents, bioremediation agents, meat tenderizing products, wound debridement and other therapeutical uses.

For a better understanding of the present invention, reference is made to the following description and its scope will be pointed out in the appended claims.

DETAILED DESCRIPTION OF THE INVENTION

In the present invention an enzyme-bearing matrix can be formed by subjecting carrier feedstock and an enzyme to conditions of temperature and shear to form the matrix. This can be accomplished by melt-spinning the enzyme with carrier materials. The matrix is included in various enzyme-based products such as leavening agents, alcohol fermenters, detergents, diagnostic agents, degradation products, petroleum hydrocarbons degraders, digestive aids, therapeutic enzymes, etc.

The spinning process can be carried out with "cotton candy" fabricating-type equipment. The spinning machine used in the present invention can be a cotton candy-type machine, such as the Econo Floss model 3017 manufactured by Gold Medal Products Company of Cincinnati, Ohio. It will be appreciated by those skilled in the art that any apparatus or physical process which provides similar forces and temperature gradient conditions can also be used. For simplicity in disclosing and describing this invention, the term "melt-spinning" will be understood to mean a process which includes a combination of temperature, shear, flow, flow rate, mechanical forces and thermal gradients of the type produced by a cotton candy-type machine.

The apparatus is operated at a temperature and speed which induce flash flow of certain carrier feedstocks without deterioration of the feedstock and enzyme(s) being processed. The resulting matrix is in the form of a floss, fibre, particle, flake, spicule, or other generally non-descript aggregate capable of protectively carrying and delivering an enzyme.

The process for producing the matrix includes introducing a mixture containing an enzyme and a carrier material simultaneously to conditions of elevated temperature and shear created by centrifugally forcing the ingredients through orifices. The extremely short amount of time the ingredients are exposed to the elevated temperature and shear allows the matrix to be formed without adverse effects.

The flash flow phenomena occurs when a solid carrier material mixed with an enzyme is subjected to conditions of melt-spin sufficient to provide internal flow. This condition produces the transformation in physical and/or chemical structure without degradation of the material. Internal flow occurs when the infrastructure of the material breaks down sufficiently to permit movement of material at a subparticle level, and probably at a molecular level. At a molecular level, internal flow contemplates the movement of molecules relative to each other.

Internal flow of material is generally associated with melting point or glass transition point. However, it is contemplated that the combined application of heat and external force is sufficient to produce flow at temperatures below the melting or glass transition point for most compositions.

The enzymes dispersed in the matrix are selected from animal-derived, plant-derived and microbially-derived preparations. These enzymes can be used as part of a leavening product, an alcohol fermenter, a detergent, a clinical diagnostic agent or a bioremedient and possibly mixtures thereof. A nonlimiting list includes amylases, proteases, invertases, oxidases, catalases, pectinases, lipases, lactases, cellulases and mixtures thereof.

In one aspect of the present invention, the matrix may be formed by mixing the carrier material with degradation enzymes such as cellulases, cutinases, lipases and pectinases and mixtures thereof. Cellulase sources include those originating in the genera Trichoderma, Penicillium, Aspergillus, Clostridium, etc. Additional cellulases can include commercially available products. Such cellulases are capable of degrading the water insoluble cellulose polymer which is part of the surface membrane of fruits and vegetables.

Cutinase sources include those originating in the genera Pseudomonas, Fusarium, Botrytis, Ulocladium, etc. Additional cutinases can include commercially available products. Cutinases are capable of degrading water insoluble cutin polymer which may be present as part of the surface membrane of fruits or vegetables.

Lipase sources include those originating in the genera Staphylococcus, Candida, Rhizopus, etc. Additional lipases can include commercially available products. Such lipases are capable of degrading water insoluble glycerol components comprising part of the surface membrane of fruits or vegetables.

Pectinase sources include those originating in the genera Rhizopus, Penicillium, Aspergillus, etc. Additional pectinases can include commercially available products. Such pectinases are capable of degrading the water insoluble pectin components comprising part of the surface membrane of fruits or vegetables.

The enzyme bearing matrix of the invention has many uses. For example, a cellulase matrix may be used to increase the permeability of the surface membrane of fruits and vegetables. The increased water permeability across the surface membrane permits easier delivery of substances such as flavorings, sweeteners, stabilizers and preservatives to the interior of the fruit or vegetable. Additionally, the increased water permeability allows for a more efficient method of dehydration of fruits and vegetables. More importantly, the use of naturally produced degradation enzymes as permeability enhancers replaces the use of chemicals such as methanol, chloroform or alkali metal hydroxides, which, if ingested, pose potential harmful side effects to consumers of fruits and vegetables.

Another important use for the enzyme carrier matrix of this invention is in the preparation of clinical diagnostics products. A nonlimiting list of active ingredients found in clinical diagnostic products include ascorbic acid oxidase, α-glycerophosphate oxidase, lactate oxidase, uriase, cholesterol esterase, cholesterol ester hydrolase, creatinine amino hydrolase, lipase, glycerol kinase, and mixtures thereof.

The clinical enzyme products contemplated herein are particularly well-suited for use with the matrix of the invention when it is desired to disperse the dry powder enzymes in aqueous liquids. It should be readily apparent to the skilled artisan that all of the active ingredients may also be provided in dry or lyophilized form and reconstituted with water prior to use. Compositions of this type are clearly contemplated by this invention. Clinical diagnostic enzymes carried in the matrix of the invention can also be incorporated into single-layer or multi-layer analytical elements of the types known in the prior art.

In another aspect of this invention, the matrix may be used to enhance the shelf-life and activity of enzymes used in immunoassays. For example, when horseradish peroxidase was spun with the matrix of the invention, the enzyme exhibited a longer shelf-life, and became more readily active.

Another class of enzyme products according to the invention are improved detergent enzymes. Detergent enzymes are known in the art as enzymes which attack stains or soiled areas of fabrics. Suitable categories of active detergent enzymes found in improved detergents include proteases, lipases, amylases, and mixtures thereof. The preferred detergent enzymes are proteases such as subtilisin and amylases such as those derived from the bacillus species.

The new matrix can be used alone or in combination with other ingredients as a means for dispersing the added ingredients throughout the material. For example, particles, chips, flakes, spicules or combinations thereof can be used to disperse enzymes which are otherwise relatively non-dispersable because of the physical characteristics of such materials. Thus, the matrix of the invention can be used to carry detergent. enzymes to be dispersed more easily and uniformly in other materials present in detergent formulations, such as surfactants, builders, whitening agents, bleaching agents and the like.

In certain embodiments the enzymes are present in the host microorganism such as in fungi, bacteria or algae. Examples of host microorganisms include yeasts, bio-remediation materials and the like.

In another aspect of the invention, yeasts may be melt-spun with selected carrier materials to obtain enhanced leavening products. Yeasts are single cell microorganisms containing enzymes which are employed in large scale fermentation processes. The commercial production of fermented beverages, foods, production of vitamins, alcoholic fermentation, antibiotic producing fermentations, all require yeasts or their enzymes to produce products simpler than the starting material. Regardless of the substrate used or the chosen microorganism, industrial fermentations require various nutrients for growth including carbohydrates, nitrogen-containing compounds, growth factors, vitamins and minerals. In most fermentations, these nutritional requirements are met by including, among others, yeast products.

In the production of alcoholic beverages, cereal grains are the principal raw material. Another important ingredient is malt that is used to produce amylase. Amylases are organic enzymes that change grain starch into maltose. In fermentation, zymase which is produced by yeasts converts the amylase produced maltose into ethyl alcohol and carbon dioxide. Saccharomyces cervisiae is the most common type of yeast used in alcoholic fermentation to generate zymase.

In fermentation processes desired metabolic changes frequently occur in a narrow temperature and pH range. Accordingly, to increase product yields, it is important to deliver yeasts having enzymatic activity in a narrow temperature and pH range. In addition, to optimize product yields, the yeasts must be rapidly and uniformly dispersable in the target liquid. Thus, yeasts suspended in the matrix of the invention are easily dispersable in the nutrient medium and have been found, in some cases, to be more readily active.

In another aspect of this invention, the matrix may be used to enhance the shelf-life and activity of enzymes used in yeasts. For example, when Fleischman's dry yeast was spun with the matrix of the invention, the yeast exhibited a longer shelf-life and became more readily active.

Another significant use for the enzyme carrier matrix of the invention finds application in the biodegradation of petroleum hydrocarbons. Many species of bacteria, fungi and algae have the enzymatic capability to use petroleum hydrocarbons as food. The bacteria genera most frequently isolated as hydrocarbon degraders are Pseudomonas, Acinetobacter, Flavobacterium, Brevibacterium, Corynebacterium, Arthrobacter. The fungus genera include Candida, Cladosporium, Trichosporium and Rhodotorula. These bacteria and fungi are present in the environment. Genetically engineered bacteria which have the enzymatic capability of degrading several groups of hydrocarbons can also be used as petroleum biodegraders.

Using the matrix of the invention, it is possible to disperse rapidly and uniformly these biodegrading agents and their nutrients into an otherwise hydrophobic or immiscible environment. In this manner the microbial cleanup of oil spills occurs more rapidly.

In yet another aspect of this invention, the enzyme carrying matrix may be used in the field of enhanced oil recovery. Microbial products, as well as viable microorganisms, suspended in the matrix may be used as stimulation agents to enhance oil recovery from petroleum reservoirs. For example, a strain of Acinetobacter calcoaceticus produces emulsan, a lipopolysaccharide used to stabilize oil in water emulsions. Xanthomonas campestris is a microbial product producing xanthan, a polysaccharide used as a water flood thickening agent in oil recovery. Both these microbial products become easily miscible in petroleum reservoirs when delivered with the matrix of the invention. The result is enhanced oil recovery.

The ability of microorganisms to use petroleum as food also has detrimental effects. For example, petroleum fuels cannot become contaminated with water or microorganisms during storage. Such contamination poses a serious problem for kerosine based jet aircraft fuels. To diminish this problem, antimicrobials that concentrate at the oil/water interfaces may be used to reduce the rate of microbial contamination of hydrocarbons. Antimicrobial organisms may be delivered at the oil/water interfaces by using the matrix of the invention.

The carriers used in the invention can be any material capable of being processed to form a matrix which can protectively suspend the enzyme for storage and/or selective delivery to the site and/or environment for release and activation. Carrier materials contemplated for use may be saccharide based, thermoplastic polymers, biodegradable polymers, and/or water soluble cellulosic material and mixtures thereof.

A non-limiting list of suitable saccharide carriers include sucrose, lactose, fructose, dextrose, sorbitol, mannitol, maltose, synthetically-derived saccharide materials such as polydextrose, and the like and mixtures thereof. Alternative saccharide materials such as maltodextrins and/or corn syrup solids are also useful. Please note that for purposes of this invention, applicant refers to maltodextrins and corn syrup solids (as defined by the FDA) collectively as maltodextrins.

Suitable thermoplastic polymers can include polypropylene, polystyrene, polyethylene, polyvinyl acetate, polyvinyl alcohol, poly(methacrylate), polyacrylic resins, lactide/glycolide copolymer and mixtures thereof. Suitable water-soluble cellulosic materials can include methylcellulose, ethylcellulose, hydroxymethyl or ethylcellulose, alkali-metal salts or carboxymethylcelluloses and the like and mixtures thereof.

In a preferred embodiment of this invention, maltodextrin has been selected as possessing unique properties as carrier material for the matrix of the invention. Maltodextrins are composed of water-soluble glucose-based polymers obtained from the reaction of starch with enzymes or acid in the presence of water. The hydrolysis reaction produces a carbohydrate mixture of saccharides having a dextrose equivalence (D.E.) of less than 40. In one embodiment of the invention, the D.E. is between 20 and 40. (These maltodextrin products have been classified by the FDA as corn syrup solids). In another embodiment, the D.E. is between 10 and 20. The maltodextrins useful in the present invention include some products sold under the trademark MALTRIN® by the Grain Processing Corporation of Muscatine, Iowa or "Dri-Sweet" variety of maltodextrins sold by the Hubinger Company of Keokuk, Iowa. Such products are available as powders, granules or the like.

The enzyme and the maltodextrin can be combined by physically mixing the two ingredients. Ingredients can be combined using a blender or any technique known in the art. The maltodextrin and the enzyme can also be mixed as a dispersion. The dispersion is formed by contacting the combination of ingredients with an aqueous medium. Dispersion allows the combination to be mixed with other materials so that a substantially homogenous mixture of all ingredients is obtained in the final enzyme product.

EXAMPLES

The following examples serve to provide further appreciation of the invention but are not meant in any way to restrict the effective scope of the invention.

EXAMPLE 1

A quantity of Columbo® No Fat Yogurt was placed in cheese-cloth in a refrigerator for 48 hours permitting the major portion of the water in the yogurt to drain out. The drained yogurt was then mixed with 35R corn syrup solids in the ratio of 1:9. This mixture was subjected to melt spinning with an Econo Floss® machine yielding a quantity of flakes which were thereafter maintained unrefrigerated for a period of seven days. At the end of the seven day period, the flakes were added to skim milk in the ratio of 4 teaspoons of flakes to 1 cup of skim milk. This mixture was then placed in a 110° F. environment for 24 hours.

A nice yogurt resulted from which it can be concluded that yogurt can be made in dry form by the subject process which dry form can be stored and subsequently reconstituted.

EXAMPLE 2

This example was carried out using packets of "Fleischman's" dry yeast available in any grocery store. Two packets of the yeast were mixed with 20 grams polypropylene powder obtained from Aldrich Chemical Co., Inc. After mixing, the mixture was spun in the floss machine producing a fibrous floss.

A series of three 1 pint plastic bottles were prepared. Into the first (bottle #1) was placed 10 gm of this floss after first rinsing the floss in tap water. Into the second bottle (bottle #2) was placed an equal weight of the floss but without rinsing. Into the third bottle (bottle #3) was emptied a packet of yeast. To each bottle was added 3 gm sucrose and one-half pint of tap water. Over the neck of each bottle was fastened an elastomeric balloon, and the conditions of the three balloons were observed and noted over a period of 24 hours.

It was observed that gas was evolved causing inflation of the balloons to a greater or lesser extent. Measured on a scale of 1 to 5 with 1 being minimal and 5 being maximal, the following relative balloon inflations were noted. For bottle #1 the inflations were about 3 and 4 after, respectively, 2 and 24 hours. For bottle #2 the corresponding inflations were 2 and 4, while for bottle #3 the corresponding inflations after 2 and 24 hours were 1 and 5.

From the foregoing it was established that the floss modified yeast was active more rapidly than the original unmodified yeast, that rinsing the floss accelerated the release of yeast activity from the floss, and that after 24 hours, whether initially rinsed or-not, the floss produced substantially the same amount of total activity. However, the total gas generated due to east activity derived from the floss was not quite as great as that provided by the unmodified yeast.

The yeast provided in the floss material was easily handled and ideal for mixing in a substantial mass, such as a mass of dough in a baking process or a biomass in a formation procedure.

EXAMPLE 3

Ten grams of Dri-vac Lactic culture obtained from Chris Hansen Laboratories containing *Streptococcus thermophilus* and *Lactobacillus bulgaricus* was mixed with grams of corn oil. 85 grams of Maltrin® 365 from Grain Processing Corporation (GPC) were slowly added to the mixture while mixing continued until all ingredients were blended thoroughly. One third of the final mixture was saved as an unspun control and two thirds of the final mixture was processed by flash flow in an Econo Floss® spinner at 135°–145° C. at 3600 rpm to produce spun flakes.

The following culture samples were prepared:
A. 180 grams of sterilized whole milk with 2.5 grams of the above spun flakes;
B. 180 grams of sterilized whole milk with grams of the unspun control mixture; and
C. 180 grams of sterilized whole milk with 0.25 grams of the Dri Vac Lactic culture.

The samples were cultured in a 40° C. water bath overnight. Sample A resulted in a smooth, firm and intact mass of yogurt which had a velvety smooth texture when separated into pieces with a spoon. Samples B and C produced a yogurt which had a coarse, porous texture. The mass of samples B and C was not as firm as that of Sample A. The texture of Sample A had much better mouthfeel than Samples B and C.

The addition of a proven amount of culture to the sterilized milk is much easier to obtain with the flakes than with the original lactic culture. Thus, the present invention enables the artisan to prepare a yogurt product more efficiently and with predictable results.

EXAMPLE 4

This example is carried out using packets of Fleischman's active dry-yeast available in grocery stores. The yeast was finely ground in a ceramic mortar and pestle and sieved through 60 and 80 mesh screens. Five grams of the sieved yeast were mixed with 2.5 grams of corn oil. The mixture was then added to 42.5 grams of Maltrin® 365 brand maltodextrin obtained from GPC and mixed until a homogenous yeast mixture was obtained.

The yeast mixture was processed by flash flow at 135°–140° at 3600 r.p.m. in an Econo Floss® spinning machine producing yeast bearing flakes.

Two one-pint plastic bottles were prepared. Into the first (bottle #1) was placed 10 grams of yeast-bearing flakes. One gram of the sieved yeast was placed into the second bottle (bottle #2). To each bottle was added 15 grams sucrose and one-half pint of tap water. Over the neck of each bottle was fastened an elastomeric balloon, the conditions of the three balloons were observed and noted over a period of 24 hours.

Observing the inflation of the balloons, it appears that the bottle with the flakes inflated the balloon to approximately the same extent as the bottle with the sieved yeast. However, the rate of inflation for bottle #1 was less than that for bottle #2.

The flakes produced in the present example provided a suitable medium for handling and mixing yeast in large masses such as dough for baking or a biomass undergoing fermentation.

EXAMPLE 5

95 gr. of Maltrin® 365 obtained from GPC and 0.1 gram of Horseradish Peroxidose obtained from Genzyme Diagnostics were mixed thoroughly by geometric dilution. Five grams of mineral oil was then added slowly while mixing until a uniform mixture was obtained.

The enzyme mixture was processed by flash flow at 135°–140° C. at 3600 r.p.m. on an Econo Floss spinning unit resulting in light pink flakes.

The enzymatic activity of processed and unprocessed enzyme was determined by the method entitled Peroxidase. This method was supplied by Genzyme Diagnostics. The principle of this method is the oxidation of Pyrogallol to Purpurogallin by Peroxidase. Reactivity is determined by time course ultraviolet (UV) spectrophotometry. The reaction rate is determined by the slope between 20 and 30 seconds.

The enzyme in the flakes remained active after the flash flow processing. Samples of the processed and unprocessed enzymes were held at 135° C. for one hour and analyzed for activity. The enzyme in the flake retained the same level of activity as before incubation while the unprocessed enzymes had lost about 20% of its activity. Thus, the present invention significantly enhanced the stability of the enzyme.

EXAMPLE 6

A 100 gram mixture of Maltrin® 365 from GPC and 10% w/w of the amylase enzyme Termamyl from Novo Nordisk was obtained by thoroughly mixing in a mortar and pestle assembly. The mixture was processed by flash flow at 3600 rpm and 135°–140° C. using an Econo Floss® spinning unit. The processed material was stored at 5° C. until it was analyzed for enzymatic activity.

Thereafter, a sample of the processed flakes and the unprocessed enzyme were equilibrated in an oven at 100° C. to determine stability. After four hours the enzyme in the flakes had retained substantially all its original activity while the unprocessed sample had lost over half of its original activity.

The enzymatic activity was determined by the method entitled "Manual Procedure for Determination of Alpha-Amylase Activity in Enzyme Preparations and Detergents". This method was provided by Novo Nordisk Bioindustrials, Inc. The principle of the method is to allow the alpha-amylase to degrade a starch polymer substrate. Phadebas tablets (Phadebas® Amylase Test, supplied by Pharmacia Diagnostics) are used. This material is a cross-linked water insoluble blue colored starch polymer. The tablet also contains bovine serum albumin and a buffer substance. After the tablet is suspended in water, the starch is hydrolysed by the alpha-amylase, giving soluble blue fragments. The absorbance of the resulting blue solution measured at 620 nm (UV spectrophotometry) is a function of the alpha-amylase activity.

Thus, the present invention produced an enzyme-bearing flake which remained active under equilibrated conditions set forth above for a longer period of time than the untreated enzyme.

EXAMPLE 7

A 200 gram mixture of the Maltrin® 365 from GPC and 10% w/w of the protease enzyme Alcalase from Novo Nordisk was obtained by thoroughly mixing in a mortar and pestle assembly. The mixture was processed by flash flow at 3600 rpm and 135°–140° C. using an Econo Floss spinning unit. The processed material was stored at 5° C. until it was analyzed for enzymatic activity.

Thereafter, a sample of the spun enzyme and the unspun enzyme were equilibrated in an oven at 57° C. for 21 hours to determine stability. After 21 hours, both samples retained substantially the same activity as was present in the original spun and unspun sample.

The proteolytic activity was determined by the method entitled "Determination of Proteolytic Activity Using Azocasein as a Substrate". This method was provided by Novo Nordisk Bioindustrials, Inc. The principle of the method is to allow the proteolytic enzyme to hydrolyze azocasein for 30 minutes at 40° C. Undigested protein is precipitated with trichloroacetic acid and the quantity of digested product is determined by ultraviolet (UV) spectrophotometry.

The protease enzyme remained active after flash flow processing for the same period of time as the untreated enzyme.

The products and process of the present invention have shown dramatic improvement in enzyme-handling and use art.

Moreover, while there have been described what are presently believed to be the preferred embodiments of the preferred invention, those skilled in the art will realize that changes in modification may be made thereto without departing from the spirit of the invention, and it is intended to claim also changes and modifications as forward in the true scope of the invention.

What is claimed is:

1. An enzyme product comprising a non-fibrous enzyme-bearing matrix formed by subjecting a feedstock comprising said enzyme and a solid carrier material capable of being flash flow processed to form said enzyme-bearing matrix to flash flow processing conditions which alter the physical and/or chemical structure of said carrier to form said enzyme-bearing matrix for delivery of said enzyme by said product.

2. The enzyme product of claim 1, wherein said conditions comprise subjecting said mixture simultaneously to flash heating and applied physical force.

3. The enzyme product of claim 2, wherein said conditions are created by melt-spinning said feedstock.

4. The enzyme product of claim 1, wherein said carrier material is selected from the group consisting of saccharides, thermoplastic polymers, biodegradable polymers, and water-soluble cellulosic materials.

5. The enzyme product of claim 4, wherein said saccharides are selected from the group consisting of polydextrose, maltodextrins, sucrose, lactose, dextrose, mannitol, sorbitol, glucose, maltose and mixtures thereof.

6. The enzyme product of claim 4, wherein said thermoplastic polymers are selected from the group consisting of polypropylene, polystyrene, polyethylene, polyvinyl acetate, polyvinyl alcohol, poly (methacrylate), polyacrylic resins, lactide/glycolide copolymer and mixtures thereof.

7. The enzyme product of claim 4, wherein said biodegradable polymers are selected from the group consisting of poly(cis-isoprene), aliphatic polyesters, polyurethanes and urea-formaldehyde polymers.

8. The enzyme product of claim 4, wherein said cellulosic materials are selected from the group consisting of methyl cellulose, ethyl cellulose, hydroxymethyl cellulose, hydroxyethyl cellulose, alkali metal salts of carboxy methyl cellulose and mixtures thereof.

9. The enzyme product of claim 1, wherein said enzyme is selected from the group consisting of amylases, proteases, invertases, oxidases, catalases, pectinases, lipases, lactases, cellulases and mixtures thereof.

10. The enzyme product of claim 9, wherein said enzyme is present in an amount from about 2% to about 40% by weight of the matrix.

11. The enzyme product of claim 10, wherein said enzyme is present in an amount from about 10% to about 30%.

12. The enzyme product of claim 11, wherein said enzyme is present in an amount from about 15% to about 22%.

13. The enzyme product of claim 1, wherein said enzyme is present in an amount from about 1% to about 10% by weight of said product and said enzyme is a protease.

14. The enzyme product of claim 1, wherein said enzyme is selected from the group consisting of leavening agents, fermentation agents, biodegradation products, detergent agents, immunoassay agents, clinical diagnostic agents, food digestive aids and therapeutic agents.

15. A baking dough comprising the enzyme product of claim 1, wherein said enzyme is a leavening agent.

16. A fermentation biomass comprising the enzyme product of claim 1, wherein said enzyme is a fermentation agent.

17. A yogurt product comprising the enzyme product of claim 1, wherein said enzyme is contained in a yogurt culture.

18. A detergent formulation comprising the enzyme product of claim 1.

19. The detergent formulation of claim 18, wherein said enzyme is subtilisin.

20. An enzyme product comprising a non-therapeutic enzyme-bearing matrix formed by subjecting a feedstock comprising said enzyme and a solid carrier material capable of being flash flow processed to form said enzyme-bearing matrix to flash flow processing conditions which alter the physical and/or chemical structure of said carrier to form said enzyme-bearing matrix for delivery of said enzyme from said product.

21. The enzyme product of claim 20, wherein said enzyme is selected from the group consisting of leavening agents, fermentation agents, biodegradation products, detergent agents and immunoassay agents.

22. The enzyme product of claim 20, wherein said conditions comprise subjecting said mixture simultaneously to flash heating and applied physical force.

23. The enzyme product of claim 22, wherein said conditions are created by melt-spinning said feedstock.

24. The enzyme product of claim 20, wherein said carrier material is selected from the group consisting of saccharides, thermoplastic polymers, biodegradable polymers, and water-soluble cellulosic materials.

25. The enzyme product of claim 24, wherein said saccharides are selected from the group consisting of polydextrose, maltodextrins, sucrose, lactose, dextrose, mannitol, sorbitol, glucose, maltose and mixtures thereof.

26. The enzyme product of claim 24, wherein said thermoplastic polymers are selected from the group consisting of polypropylene, polystyrene, polyethylene, polyvinyl acetate, polyvinyl alcohol, poly(methacrylate), polyacrylic resins, lactide/glycolide copolymer and mixtures thereof.

27. The enzyme product of claim 24, wherein said cellulosic materials are selected from the group consisting of methyl cellulose, ethyl cellulose, hydroxymethyl cellulose, hydroxyethyl cellulose, alkali metal salts of carboxyl methyl cellulose and mixtures thereof.

28. The enzyme product of claim 24, wherein said enzyme is selected from the group consisting of amylases, proteases, invertases, oxidases, catalases, pectinases, lipases, lactases, cellulases and mixtures thereof.

29. The enzyme product of claim 28, wherein said enzyme is present in an amount from about 2% to about 40% by weight of the matrix.

30. A baking dough composition comprising the enzyme product of claim 20, wherein said enzyme is a leavening agent.

31. A fermentation biomass comprising the enzyme product of claim 20, wherein said enzyme is a fermentation agent.

32. A yogurt composition comprising the enzyme product of claim 20, wherein said enzyme is contained in a yogurt culture.

33. A detergent comprising the enzyme product of claim 20, wherein said enzyme is a detergent enzyme.

34. The detergent of claim 33, wherein said enzyme is selected from the group consisting of proteases, lipases, amylases, and mixtures thereof.

\* \* \* \* \*